United States Patent
McFadden et al.

(10) Patent No.: US 10,322,149 B2
(45) Date of Patent: *Jun. 18, 2019

(54) MYXOMA-TREATED GRAFT MATERIAL FOR CANCER TREATMENT

(71) Applicant: University of Florida Research Foundation, Inc., Gainesville, FL (US)

(72) Inventors: Douglas G. McFadden, Gainesville, FL (US); Eric C. Bartee, Gainesville, FL (US); Christopher R. Cogle, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,438

(22) Filed: Aug. 14, 2017

(65) Prior Publication Data

US 2018/0064760 A1 Mar. 8, 2018

Related U.S. Application Data

(63) Continuation of application No. 14/124,800, filed as application No. PCT/US2012/041905 on Jun. 11, 2012, now Pat. No. 9,730,960.

(60) Provisional application No. 61/495,342, filed on Jun. 9, 2011.

(51) Int. Cl.
*A61K 35/28* (2015.01)
*A61K 35/768* (2015.01)
*A61K 35/17* (2015.01)
*A61K 35/14* (2015.01)
*C12N 5/0783* (2010.01)
*A61K 35/12* (2015.01)

(52) U.S. Cl.
CPC .............. *A61K 35/28* (2013.01); *A61K 35/14* (2013.01); *A61K 35/17* (2013.01); *A61K 35/768* (2013.01); *C12N 5/0636* (2013.01); *A61K 2035/122* (2013.01); *A61K 2035/124* (2013.01); *C12N 2710/24041* (2013.01)

(58) Field of Classification Search
None
See application file for complete search history.

(56) References Cited

U.S. PATENT DOCUMENTS

2006/0026333 A1 2/2006 Parr et al.
2009/0317362 A1 12/2009 McFadden et al.

OTHER PUBLICATIONS

Kim et al., Leukemia 23, 2313-2317 (Year: 2009).*

Annaloro,C., et al., "Autologous hematopoietic stem cell transplantation in autoimmune diseases", Expert Rev Hematology, vol. 2, Issue 6, pp. 699-715 (2009).
Blazar, B., et al, "Recent advances in graft-versus-host disease (GVHD) prevention", Immunol Rev, vol. 157, pp. 79-109, 1997. (submitted in two parts).
Burt, R., et al., "Hematopoietic stem cell transplantation for autoimmune diseases: What have we learned?", J Autoimmun, vol. 30, Issue 3, pp. 116-120 (2008).
Choi, S., et al., "Pathogenesis and Management of Graft-Versus-Host disease", Immunol Allergy Clin North Am, vol. 30, pp. 75-101 (2010).
Cogle, C., Madlambayan, G., et al., "Acute Myeloid Leukemia Cells Generate Leukemic Endothelial Cells with Leukemogenic Potential: Blood Vessels As Sanctuaries for Leukemia Relapse", Blood Journal, vol. 118 (2011).
Extended European search report for EP Application 12796051.6 dated Oct. 16, 2014, pp. 1-12.
Gallardo et al., "Is mobilized peripheral blood comparable with bone marrow as a source of hematopoietic stem cells for allogeneic transplantation from HLA-identical sibling donors? A case-control study", Haematologica, vol. 94, Issue 9, pp. 1282-1288 (2009).
Gratwohl, A., et al., "The EBMT activity survey 2006 on hematopoietic stem cell transplantation: focus on the use of cord blood products", Bone Marrow Transplant, vol. 41, 19 pages (2008).
International Search Report and Written Opinion for PCT Application PCT/US12/041905 dated Feb. 28, 2013, pp. 1-13.
Ito, R., et al., "Highly sensitive model for xenogenic GVHD using severe immunodeficient NOG mice", Transplantation, vol. 87, Issue 11, pp. 1654-1658 (2009).
Mossman, K., et al., "Myxoma Virus M-T7, a Secreted Homolog of the Interferon-γ Receptor, Is a Critical Virulence Factor for the Development of Myxomatosis in European Rabbits", (1996) Virology, vol. 215:17-30.
Nash, P., et al, "Immunomodulation by viruses: the myxoma virus story", Immunological Reviews, 1999, vol. 168, pp. 103-120.
Paczesny, S., et al., "Acute graft versus host disease: new treatment strategies", Curr Opin Hematol, vol. 16, Issue 6, pp. 427-436 (2009).
Schroeder, M., et al, "Mouse models of graft-versus-hots disease: advances and limitations", Disease Models and Mechanisms, 2011, vol. 4, pp. 318-333.
Villa, N., et al, "Myxoma virus suppresses proliferation of activated T lymphocytes yet permits oncolytic virus transfer to cancer cells", Blood Journal, 2015, vol. 125, Issue 24, pp. 3778-3788.

* cited by examiner

*Primary Examiner* — Daniel C Gamett
(74) *Attorney, Agent, or Firm* — Timothy H. Van Dyke; Beusse, Wolter, Sanks & Maire PLLC

(57) ABSTRACT

A method of treating or preventing graft versus host disease (GVHD) in a subject receiving a graft comprising hematopoietic cells is provided. The method comprises contacting the graft ex vivo with an amount of a Myxoma Virus effective to inhibit proliferation of T lymphocytes in the graft and to treat or prevent GVHD in the host subject following infusion of the graft into the subject. After the contacting of the graft with the Myxoma Virus, the method comprises transplanting the virus-treated graft into the subject.

27 Claims, 13 Drawing Sheets

MYXOMA-TREATED GRAFT MATERIAL FOR CANCER TREATMENT

CROSS-REFERENCE TO RELATED APPLICATIONS

This application is a continuation of U.S. application Ser. No. 14/124,800 having a 371(c) date of Jul. 14, 2014 and claims the benefit of PCT/US12/41905 filed Jun. 11, 2011 and U.S. Provisional Application No. 61/495,342, filed Jun. 9, 2011. These applications are incorporated herein in their entirety.

STATEMENT REGARDING FEDERALLY SPONSORED DEVELOPMENT

Development for this invention was supported in part by Contract No. R01 CA138541, awarded by the National Institutes of Health, and Contract No. R21 CA149869, awarded by the National Cancer Institute. Accordingly, the United States Government has certain rights in this invention.

FIELD OF THE INVENTION

The present invention relates to methods for treating or preventing graft versus host disease (GVHD), as well as to methods for inhibiting T lymphocyte proliferation in a biological sample, e.g., an allogeneic cell application.

BACKGROUND OF THE INVENTION

Graft-versus-host disease (GVHD) is a potentially lethal clinical complication arising from the transfer of alloreactive T lymphocytes into immunocompromised patients. Specifically, one major component of GVHD includes the transfer of mature donor $CD3^+$ T lymphocytes present in the transplanted product into the immunocompromised recipient. Once infused, donor T cells recognize host cellular antigens, resulting in an immunoreactive cascade often affecting the liver, gastrointestinal tract and skin (1,2).

Current methods to prevent and treat GVHD have included general immune suppression following transplant, reduced intensity conditioning, and depletion or inhibition of alloreactive donor T lymphocytes prior to transfusion (2, 3). The clinical effectiveness of these methods, however, is limited by a variety of side effects. For example, general immune suppression leads to an increased risk of reactivated virus infections and opportunistic infections, while reduced intensity conditioning regimens are associated with increased relapse rates (3). Currently, the most promising prophylactic treatment for GVHD is depletion or inhibition of donor T lymphocytes. This can be accomplished through a variety of methods including lymphoablative cytotoxic agents, specific T lymphocyte inhibitors, and T cell depletion by selecting for $CD34^+$ hematopoietic stem and progenitor cells (HSPC or HSPCs). These methods have proven effective at lowering the rates of GVHD; however, they are also associated with slower reconstitution of the recipient immune system, increased risk for life-threatening infections and potentially limited graft-versus-leukemia effect (4, 5).

DETAILED DESCRIPTION OF THE INVENTION

Figures 1A, 1B:
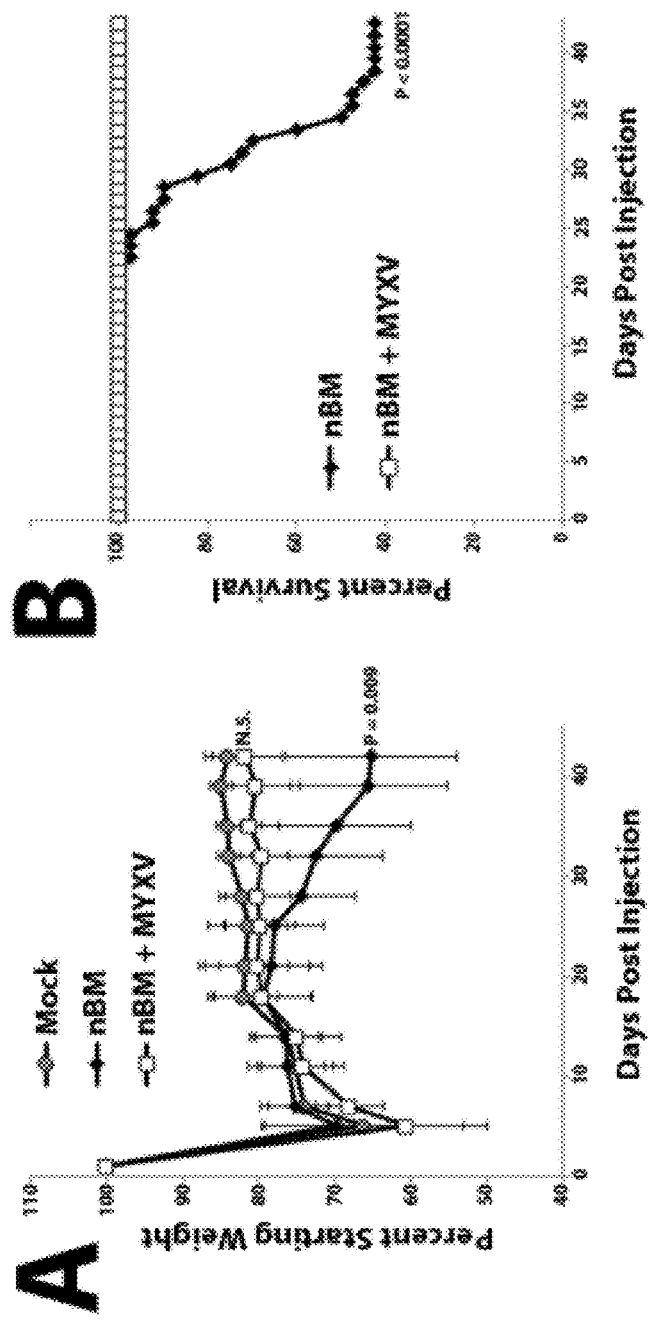
FIG. 1A-C: Myxoma Virus (MYXV)-treatment prevents lethal GVHD. NSG mice were sublethally irradiated and then transplanted with either PBS (mock, n=5), $1 \times 10^7$ primary human bone marrow (BM) (n=36) or $1 \times 10^7$ primary human BM pre-treated with MYXV (n=36). Mice were weighed twice per week to monitor body condition (A) and sacrificed either six weeks after transplant or when they reached a body condition score of 2 (B). Significant differences in survival were determined using the log-rank test (P<0.05). N.S.=not significant. Post-mortem, organs were extracted, fixed in formalin, sectioned and stained for the presence of human $CD3^+$ lymphocytes (C). Immunohistochemistry images shown are representative of results observed in five separate mice.
Figure 1C:
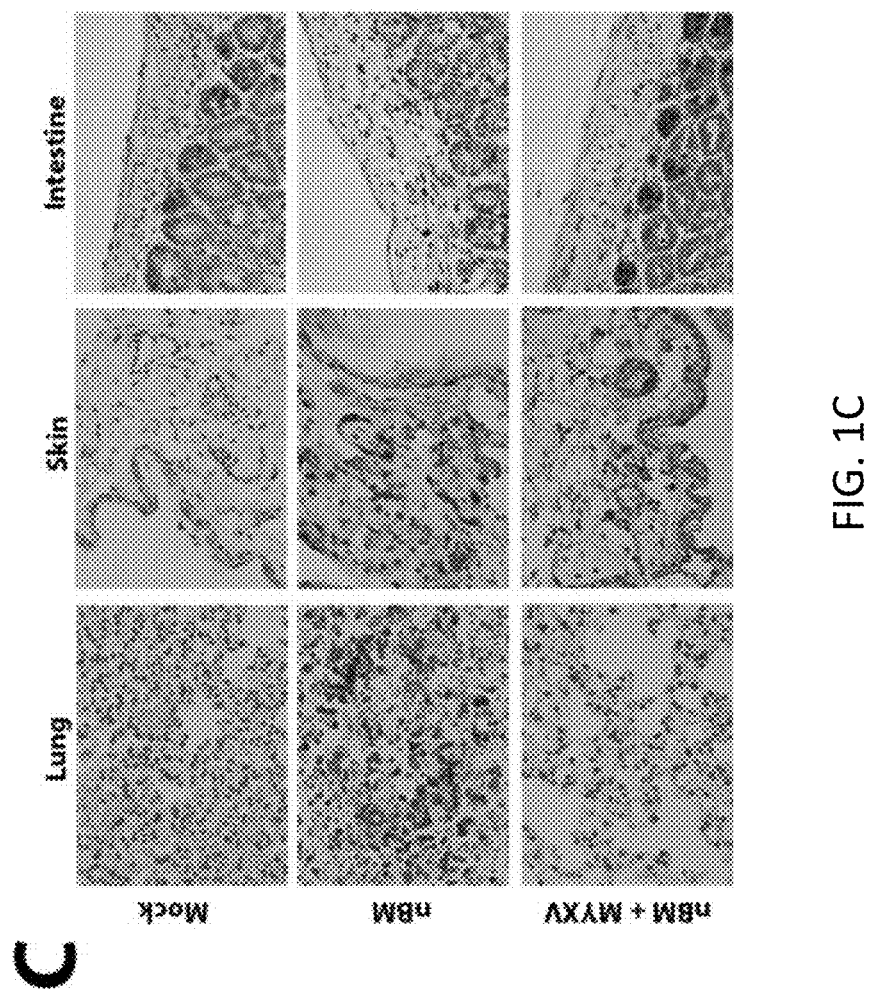

The present inventors have found that treatment of biological samples, such as allogeneic cells, with Myxoma Virus purges or inhibits expansion of T lymphocytes present in the biological samples. In this way, an allogeneic graft treated with Myxoma Virus prevents GVHD. Without the Myxoma Virus treatment described herein, alloreactive T lymphocytes in the graft may cause damage to several vital organs, including the liver, intestines, skin, and lungs of the recipient. This damage may range from mild inflammation to destruction of the mucosa of the intestine to fatal exfoliation of target cells. Inflammation typically presents as fever, abdominal pain, nausea, vomiting, diarrhea, intestinal bleeding, and jaundice.

As used herein, the terms "biological sample" or "sample" refers to a biological material that is isolated from its natural environment. The sample may comprise a tissue sample, a biological fluid sample (e.g., blood, plasma), or a cell sample, e.g., a hematopoietic cell sample. The sample may be obtained from a donor individual by any suitable technique known in the art, a tissue bank, or other source prior to transplant into a recipient host subject.

As used herein, the term "contacting" refers to and includes any method for exposing or placing a biological sample to the Myxoma virus.

As used herein, the term "effective amount" means an amount effective at dosages and for periods of time necessary to achieve the desired result.

As used herein, the term "Graft Versus Host Disease" or "GVHD" refers to the pathological reaction that occurs between the grafted tissue and the host-recipient. Graft-versus-host-disease (GVHD) often occurred following hematopoietic cell and solid organ transplantation. In GVHD, alloreactive T lymphocytes recognize the recipient's tissues as foreign. Thus, they attack and mount an inflammatory and destructive response against the recipient. GVHD has a predilection for epithelial tissues, especially skin, liver, and mucosa of the gastrointestinal tract. GVHD, itself, is a profoundly immunocompromised state given that the immune system is involved in a large-scale alloimmune response. In addition, subjects with GVHD are often treated with powerful immunosuppressant agents, thereby making them even more susceptible to opportunistic infectious agents.

As used herein, the term "graft" refers to a sample, e.g., a hematopoietic cell sample, which is introduced into a subject as defined herein. The graft may be an allogeneic graft or an autologous graft.

As used herein, the term "hematopoietic cell" as used herein means any type of cell of the hematopoietic system, including, but not limited to, undifferentiated cells such as hematopoietic stem cells and progenitor cells (HSPCs), and differentiated cells such as megakaryocytes, platelets, erythrocytes, leukocytes, granulocytes, monocytes, lymphocytes, and natural killer (NK) cells.

As used herein, the term "hematopoietic cell transplantation" includes and refers to blood and bone marrow transplantation, peripheral blood stem cell transplantation, donor cell infusion, umbilical cord blood transplantation, or any other source of multipotent hematopoietic stem cells.

As used herein, the term "host subject" or "subject" refers to any individual member of the animal kingdom, including humans. In one embodiment, the subject is any mammal that is to, is, or has received a graft as described herein. A mammalian subject may include, but is not limited to humans, monkeys, horses, pigs, cows, dogs, cats, rats, and mice. In a specific embodiment, the methods of the present invention are employed to treat a human subject.

As used herein, the terms "immunocompromised," "immunocompromised subject" or "immunocompromised individual" refer to a subject who is at risk for developing infectious diseases because the immune system of the subject is not working at optimum capacity. In one embodiment, the subject is immunocompromised due to a treatment regimen designed to treat an underlying disease and/or prevent rejection of a graft, for example.

As used herein, the phrase "inhibiting the proliferation of T lymphocytes" refers to the purging or deletion of T lymphocytes from the subject biological sample and/or the inhibition of the proliferation of T lymphocytes in the biological sample.

As used herein, the term "nonpathogenic virus" means that the virus, e.g., Myxoma virus, is not pathogenic to a subject of interest. In other words, the Myxoma virus does not cause disease in the subject.

As used herein, the terms "prevent" or "preventing" refers to halting, delaying and/or reducing the severity of the symptoms associated with GVHD.

As used herein, the terms "treat" or "treating" refers to an approach for obtaining beneficial or desired results, including clinical results. Beneficial or desired clinical results can include, but are not limited to, alleviation or amelioration of one or more symptoms or conditions, diminishment of extent of disease, e.g., GVHD, stabilization of the state of disease, prevention of development of disease, prevention of spread of disease, delay or slowing of disease progression, delay or slowing of disease onset, amelioration or palliation of the disease state, and remission (whether partial or total), whether detectable or undetectable. "Treating" can also mean prolonging survival of a patient beyond that expected in the absence of treatment. Further, "treating" can also mean inhibiting the progression of disease, slowing the progression of disease temporarily, although more preferably, it may include halting the progression of the disease permanently. As will be understood by one skilled in the art, results may not be beneficial or desirable if, while improving a specific disease state, the treatment results in adverse effects on the subject treated that outweigh any benefits produced by the treatment.

As used herein, the term "transplant" as used herein refers to any organ or body tissue that has been transferred from its site of origin to a recipient site, or the act of doing so. The term "transplant" includes but is not limited to transfer by injection, topical application, and/or filling.

In accordance with one aspect of the present invention, there is provided a method of treating or preventing GVHD in a subject receiving a graft comprising hematopoietic cells. The method comprises contacting the graft ex vivo with an amount of a Myxoma virus effective to inhibit proliferation of T lymphocytes in the graft and to treat or prevent GVHD in the subject following transplant of the graft into the subject. In addition, the method comprises, after the contacting of the graft with the Myxoma virus, transplanting the virus-treated graft into the subject. The transplanting may comprise any suitable technique known in the art, such as allogeneic hematopoietic cell transplant, a donor cell infusion, and a supportive blood product transfusion. In one embodiment, the infusion is done as a haploidential transplant.

In accordance with one aspect of the present invention, there is provided a method for inhibiting the proliferation of T lymphocytes in a biological sample. The method comprises contacting the biological sample with an amount of Myxoma Virus effective to inhibit the proliferation of T lymphocytes in the biological sample. In one embodiment, the Myxoma Virus acts to inhibit the proliferation of $CD3^+$ T lymphocytes from the biological sample or graft.

The biological sample comprising the hematopoietic cells may be obtained from a subject via any standard procedure known in the art, including but not limited to biopsy and aspiration. For example, one can collect hematopoietic cells by apheresing patients with or without cytokine mobilization. Typically, the biological sample is maintained at a temperature of from about 35° C. to about 38° C. for a period of 30-120 minutes, and preferably 60 minutes to stabilize the sample before introducing the poxvirus to the sample. Once treated with the nonpathogenic poxviruses of the present invention, the treated hematopoietic cells may be returned or administered to the patient using any known technique known in the art. For example, one can re-infuse the cells via intravascular administration or directly back into the patient's systemic circulation.

In accordance with yet another aspect of the present invention, there is provided a cell population comprising a plurality of hematopoietic cells treated with an amount of a Myxoma virus.

The Myxoma virus used herein may be any virus that belongs to the Leporipoxvirus species of poxviruses. The Myxoma virus may be a wild-type strain of Myxoma virus or it may be a genetically modified strain of Myxoma virus. The Myxoma virus may be prepared and formulated according to any known method and formulation known in the art, including as set forth in U.S. Published Patent Application No. 2006/026333, the entirety of which is incorporated by reference. For example, the Myxoma virus may be prepared by infecting cultured rabbit cells with the Myxoma virus strain that is to be used, allowing the infection to progress such that the virus replicates in the cultured cells and can be released by standard methods known in the art for disrupting the cell surface and thereby releasing the virus particles for harvesting. Once harvested, the virus titer may be determined by infecting a confluent lawn of rabbit cells and performing a plaque assay (see Mossman et al. (1996) Virology 215:17-30). It is important to note that Myxoma virus' host tropism is highly restricted to European rabbits, and it is nonpathogenic for all other vertebrate species tested, including humans (McFadden, 2005). Its genome is non-segmented and contains a single molecule of linear double-stranded DNA, 160,000 nucleotides in length. The genome has a G-C content of ~40% with terminally redundant sequences that is repeated at both ends.

When contacting a biological sample with the Myxoma virus, one skilled in the art would readily be able to determine the amount and duration of the treatment suitable to achieve the desired result. In one embodiment, the biological sample is an allogeneic graft and is treated with a Myxoma virus for a period of at least an hour, e.g. three hours. In addition, the biological sample may be treated with an effective amount of the Myxoma virus, which may be measured by the multiplicity of infection (MOI) in the sample. The MOI is the ratio of infectious agents (e.g., phage or virus) to infection targets (e.g., cell). For example, when referring to a group of cells inoculated with infectious virus particles, the MOI is the ratio defined by the number of infectious virus particles deposited in a well divided by the number of target cells present in that well. In one embodiment, the MOI used when contacting a sample, e.g., an allogeneic graft, with the Myxoma virus is about 10.

In one embodiment, the graft to be treated with the Myxoma virus may comprise bone marrow or human peripheral blood cells having a plurality of hematopoietic cells. In a particular embodiment, the graft is an allogeneic graft.

It is further appreciated that ex vivo treatment of the graft to be introduced into a patient may be performed in combination with other therapies, including chemotherapy, radiation therapy or other anti-viral therapies. In one embodiment, the graft treated with the Myxoma virus can be transplanted into a subject in combination with, or in a sequential fashion with, other oncolytic viruses, which may demonstrate specificity for varying tumor cell types.

In accordance with another aspect of the present invention, there is provided a method for treating cancer in a subject. The method comprises contacting a graft comprising a plurality of hematopoietic cells with an amount of a Myxoma Virus ex vivo effective to inhibit proliferation of T lymphocytes in the graft. In addition, the method comprises administering to the host subject at least one treatment from the group consisting of chemotherapy, biotherapy, immunosuppression and radiotherapy to the host subject. Thereafter, the method comprises transplanting the virus-treated graft into the subject. In one embodiment, the graft comprises bone marrow or human peripheral blood cells.

Treatment of cancers that are currently considered treatable, or potentially treatable, by hematopoietic stem cell transplantation via either self-donors (autologous transplants) or matched-donors (allogeneic transplants) are provided herein. Exemplary cancers and/or cancer cells treatable by the present invention include, but are not limited to cells derived from patients having hematopoietic malignancies such as lymphomas, myelomas, leukemias, myelodysplastic syndromes, neuroblastoma, sarcomas, lung cancer, small cell lung cancer, breast cancer, colorectal cancer, pancreatic cancer, brain cancer, ovarian cancer and gastric cancer. In one embodiment, the methods described herein are used with subjects having a hematological malignancy. The hematological malignancy may be a leukemia, a myelodysplastic syndrome, a lymphoma, or a myeloma. In a particular embodiment, the cancer is one of acute myeloid leukemia (AML) or multiple myeloma (MM). In one embodiment, the cancer is refractory cancer, e.g., a cancer that does not respond to treatment or has become resistant to treatment. Other treatable cancers include Hodgkins disease, non-Hodgkins lymphomas, acute lymphocytic leukemia, aplastic anemia, chronic myelogenous leukemia, and various unclassified leukemias.

In the methods described herein, any suitable technique for chemotherapy, biotherapy, immunosuppression and radiotherapy known in the art may be used. For example, the chemotherapeutic agent may be any agent that exhibits an oncolytic effect against cancer cells or neoplastic cells of the subject. For example, the chemotherapeutic agent may be, without limitation, an anthracycline, an alkylating agent, an alkyl sulfonate, an aziridine, an ethylenimine, a methyhnelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent is one that is known to be effective against the particular cell type that is cancerous or neoplastic. In one embodiment, the chemotherapeutic agent is effective in the treatment of hematopoietic malignancies, such as thiotepa, cisplatin-based compounds, and cyclophosphamide. Cytokines would include interferons, G-CSF, erythropoietin, GM-CSF, interleukins, parathyroid hormone, and the like. Biotherapies include rituximab, bevacizumab, vascular disrupting agents, lenalidomide, and the like. Radiosensitizers include nicotinomide, and the like.

While aspects of the present invention are directed to the ex vivo treatment of a biological sample, e.g., graft, it is appreciated that the Myxoma virus may also be administered to a subject in vivo as set forth in U.S. Published Patent Application No. 20090317362 to McFadden et al., the entirety of which is incorporated by reference herein. Within vivo use, the Myxoma virus may be formulated as an ingredient in a pharmaceutical composition. It is understood the compositions may routinely contain pharmaceutically acceptable concentrations of salt, buffering agents, preservatives and various compatible carriers. For all forms of delivery, the Myxoma virus may be formulated in a physiological salt solution. The pharmaceutical compositions may additionally contain other therapeutic agents, such as anticancer agents. In various embodiments, the compositions include chemotherapeutic agents, cytokines, biotherapeutic agents, and radiosensitizers.

It is further appreciated that the methods described herein may be utilized to treat non-malignant disorders characterized by pathogenic and/or auto-reactive T lymphocytes, such as autoimmune disorders. Thus, in accordance with another aspect of the present invention, there is provided a method for treating a T lymphocyte-mediated autoimmune disorder. The method comprises contacting a graft comprising a plurality of hematopoietic cells with an amount of a Myxoma Virus ex vivo effective to inhibit proliferation of T lymphocytes in the graft. In addition, the method further comprises transplanting the virus-treated graft into the subject. In this way, the method has the potential to be used to delete and/or inhibit pathogenic, auto-reactive T lymphocytes that cause autoimmune disorders, such as multiple sclerosis.

The following example(s) are intended for the purpose of illustration of the present invention. However, the scope of the present invention should be defined as the claims appended hereto, and the following example(s) should not be construed as in any way limiting the scope of the present invention.

Example 1

In the following Example, the following materials and methods were used.

Normal Human Cells: Fresh normal human bone marrow aspirate cells and peripheral blood mononuclear cells were obtained from Lonza. Bone marrow mononuclear cells were then enriched over a Ficoll gradient using a clinical Sepax device (Biosafe Inc.) as per manufacturer's recommendations.

Myxoma virus and viral Infections: All viral infections were carried out by incubating cells with vMyx-GFP, a MYXV construct which expresses eGFP at an intergenic location in the viral genome from a synthetic viral early/late promoter (21). This construct allows the early stages of viral replication to be detected based on GFP expression within test cells. Human bone marrow cells were exposed to vMyx-GFP at a multiplicity of infection (MOI) of 10 for 3 hours in PBS+10% FBS in a humidified chamber at 37° C. and 5% $CO_2$. Mock treated cells were incubated in PBS plus 10% FBS containing no virus under the same incubation conditions.

Stem Cell Xenografts: For GVHD studies, NOD/Scid/ $IL2R\gamma^{-/-}$ (NSG) mice were sublethally irradiated using 200 cGy total body irradiation from a $Cs^{137}$ source. Within twenty-four hours after irradiation, mice were injected through the tail vein with $1\times10^6$-$10\times10^6$ cells that had been either mock treated, treated, or contacted with vMyx-GFP. Prophylactic antibiotics were administered in the drinking water for two weeks after transplantation to prevent opportunistic bacterial infection. Six weeks after transplantation, mice were euthanized and bone marrow was harvested. Human stem cell engraftment was quantified using flow cytometry (BD FACSCaliber) for human $CD45^+$ and HLA-A,B,$C^+$ cells. Mice were scored as engrafted if flow cytometry confirmed populations of cells present in bone marrow that were human $CD45^+$/HLA-A,B,$C^+$ double positive. The number of $CD45^+$/HLA-A,B,$C^+$ cells in each bone marrow sample is presented as level of engraftment. Lineage analysis of engrafted cells was determined by co-staining extracted murine bone marrow with the following antibodies: HLA-APC, CD3-PE, CD19-FitC, CD15-PERCP.

Immunohistochemistry: Analysis of infiltration of human cells into murine peripheral tissues was accomplished by surgically removing six tissues post mortem: lung, liver, kidney, spleen, skin, and intestine. Tissues were fixed in 10% formalin buffered with PBS for 24 hours and then washed in 70% EtOH for an additional 24 hours. Five-micron sections of formalin-fixed, paraffin-embedded blocks were cut and picked-up onto plus charged slides (Fisher Scientific). Slides were deparaffinized and rehydrated through a series of xylenes and graded alcohols and blocked in 3% peroxide/methanol for 10 minutes at RT. Heat mediated antigen retrieval was performed in Citra buffer pH6.0 for 25 minutes. This was immediately followed by blocking with normal goat serum and avidin/biotin using a commercially available kit (Vector Labs). Rabbit anti-CD 3 was applied to the sections at 1:100 overnight at 4 C. Staining was completed using an ABC-Elite kit (Vector Laboratories). The antigen-antibody complex was observed by reaction with DAB (Vector Labs) and slides were counterstained with hematoxylin prior to coverslipping.

Magnetic activated cell sorting: $CD3^+$ and $CD34^+$ cells were fractionated from SEPAX purified normal bone marrow aspirates using the $CD3^+$ (Cat#130-050-101) and $CD34^+$ (Cat#130-046-702) microbead separation kits from Miltenyi Biotec as per manufacturer's recommendations. Cells were then separated on an autoMACS pro separator (Miltenyi Biotec) as per manufacturer's recommendations. The relative purity of each fractionated population was confirmed after separation using flowcytometry. The total number of fractionated cells was determined after separation using a hemocytometer.

Figures 2A, 2B:
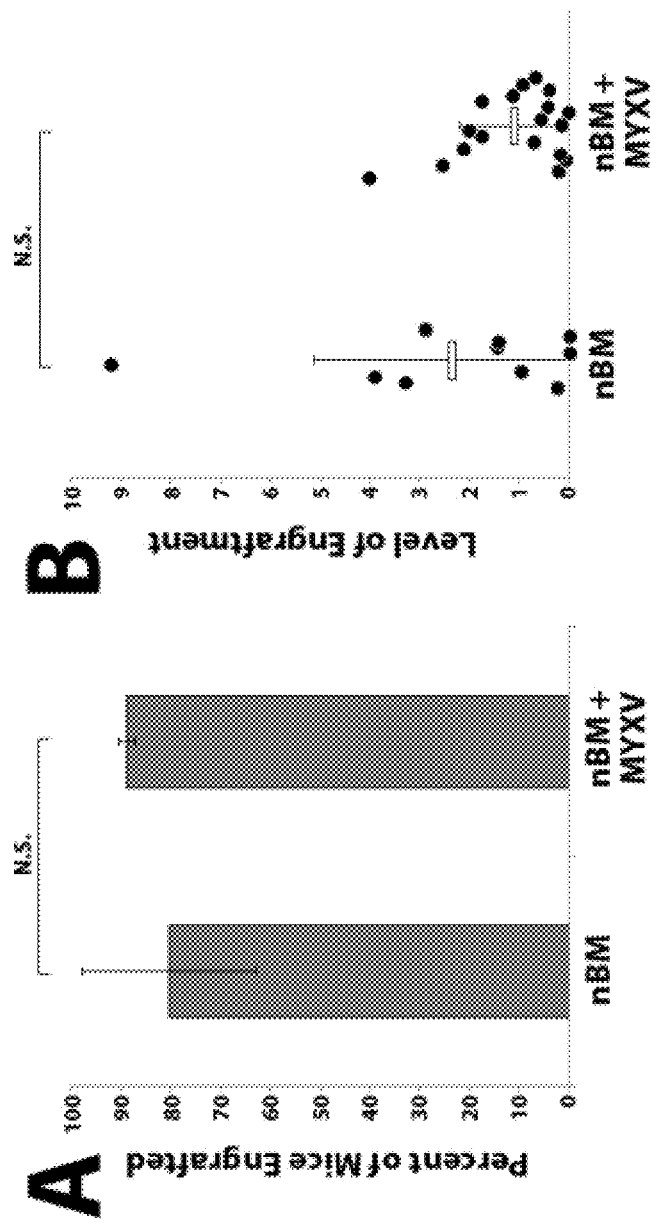
FIG. 2A-F: MYXV treatment prevents in vivo expansion of donor T lymphocytes after transplant and permits engraftment of normal HSPCs. NSG mice were sublethally irradiated and transplanted with $1 \times 10^7$ whole BM cells. Six weeks after transplant, bone marrow from mice were harvested and analyzed for human hematopoietic engraftment (human $CD45^+$/HLA-A,B,$C^+$ double positive cells) by flow cytometry. Treatment with MYXV did not alter the proportion of animals with successful human hematopoietic engraftment (A) or the level of this engraftment in mice bone marrow (B). Irradiated mice transplanted with $1 \times 10^7$ CD34-depleted BM displayed lower overall levels of engraftment and this engraftment was significantly reduced by ex vivo MYXV-treatment (C). Irradiated mice transplanted with $1 \times 10^5$ $CD34^+$ selected cells showed levels of human engraftment similar to those observed in mice transplanted with whole BM. Levels of engraftment were not affected by ex vivo MYXV-treatment (D). Significance was determined using Student's t-test (P<0.05). N.S=not significant. NSG mice were sublethally irradiated and then transplanted with $5 \times 10^6$ Ficoll enriched peripheral blood mononuclear cells (PBMCs). Mice were weighed twice per week to monitor body condition (E) and sacrificed either six weeks after transplant or when their body condition score measured 2 (F). Significant differences in survival were determined using the log-rank test (P<0.05).
Figures 2C, 2D:
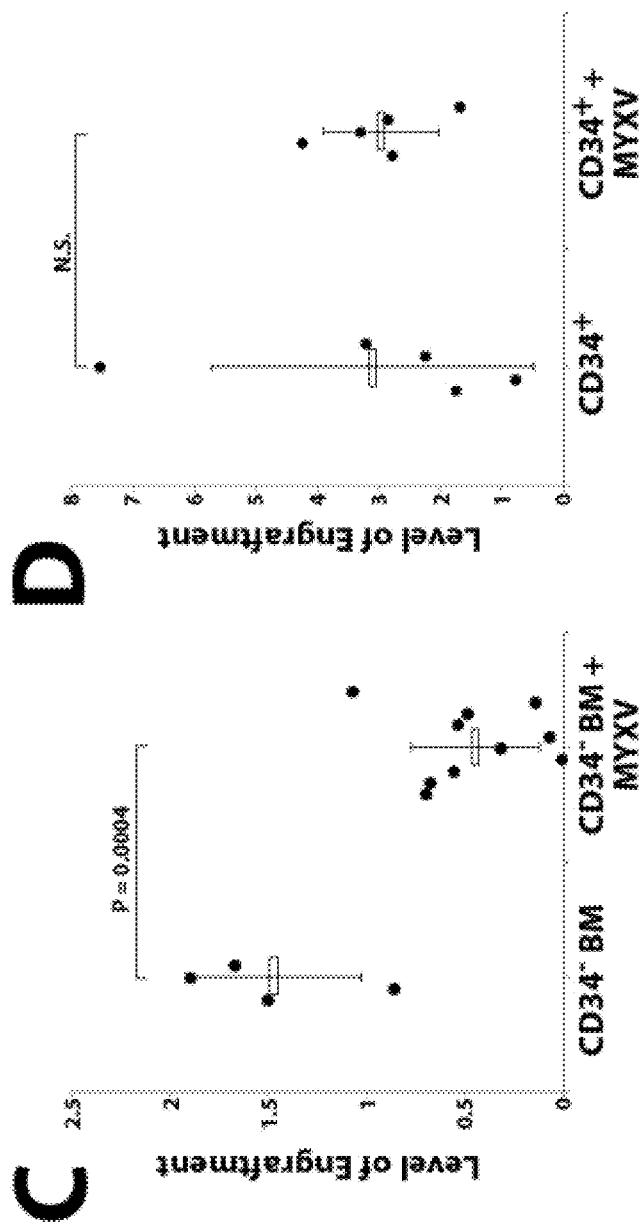
Figures 5A, 5B:
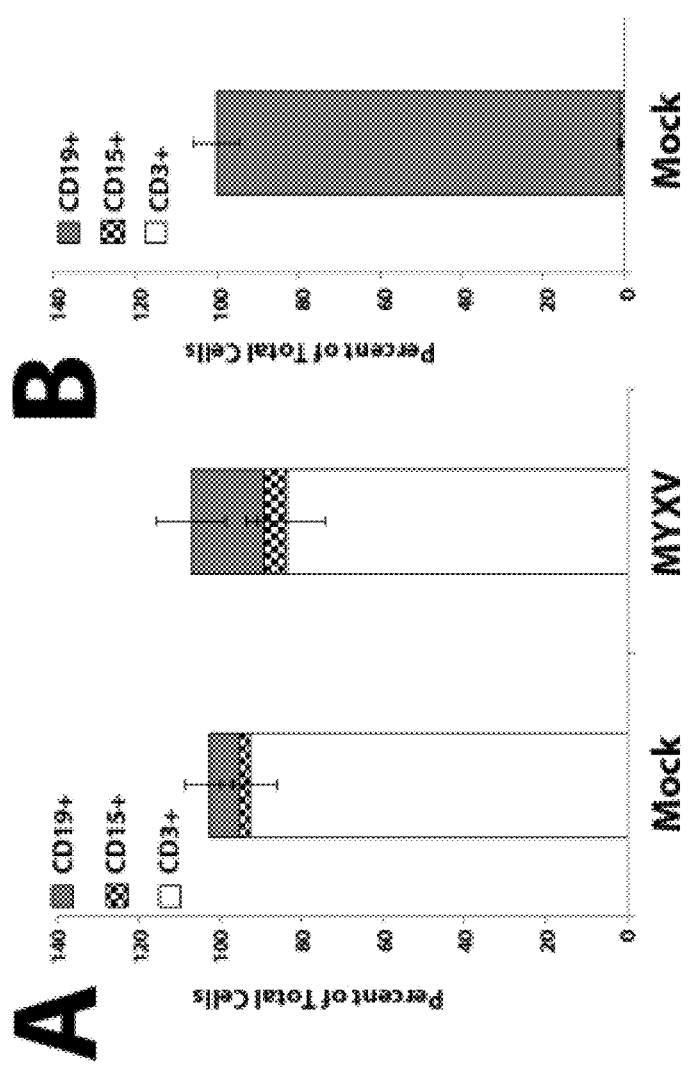
FIG. 5A-B: Mice injected with CD34+ cells or CD34+ depleted bone marrow display engraftment of distinct lymphocytic lineages. NSG mice were sublethally irradiated and then transplanted with either $1 \times 10^7$ CD34+ depleted bone marrow or $1 \times 10^5$ CD34+ selected HSPCs. Six weeks post injection, mice were sacrificed and the lineage of human cells found in the bone marrow was determined by co-staining extracted murine bone marrow with antibodies against HLA-APC, CD3-PE, CD19-FitC, CD15-PERCP. Human cells in mice injected with CD34+ depleted bone marrow were predominantly HLA+/CD3+/CD15−/CD19− cells (A) while human cells in mice injected with CD34+ selected cells were predominantly HLA+/CD3−/CD15−/CD19+ cells (B).
Figure 6:
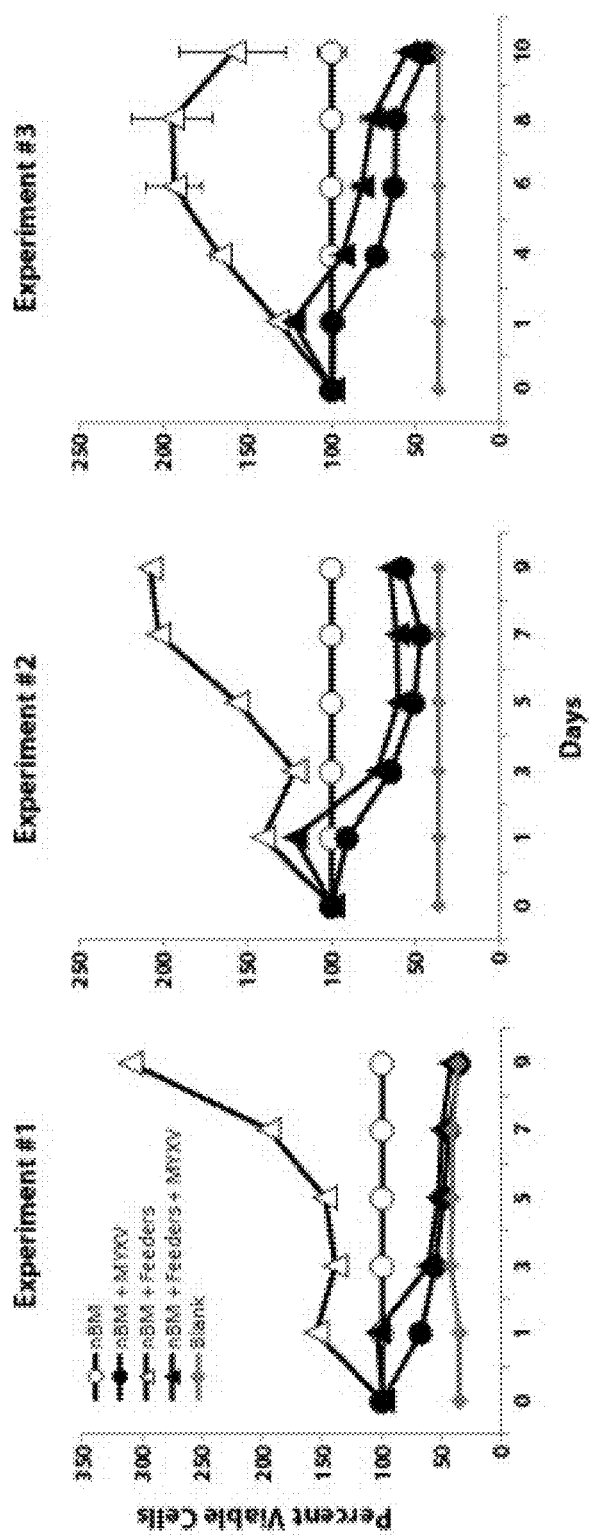
FIG. 6: MYXV treatment inhibits expansion of T lymphocytes. To determine if MYXV inhibited expansion of normal donor T lymphocytes following allo-stimulation, mock-treated of MYXV-treated BM was incubated for 10 days with irradiated HLA-mismatched feeder cells. Mock-treated BM stimulated with irradiated feeder cells demonstrated a significantly increased number of viable cells while MYXV-treated BM did not. This effect was consistent across three separate bone marrow donors.

Mixed Lymphocyte Reaction Assays: $1 \times 10^6$ SEPAX purified nBM cells were plated in triplicate into each well of a 96-well plate. Cells were then irradiated using 1000 cGy from a $Cs^{137}$ source to create replication incompetent feeder cells. SEPAX purified nBM cells from a second HLA-mismatched donor were either mock-treated or treated with MYXV and then $1 \times 10^6$ cells were plated in triplicate into empty wells or wells containing irradiated feeder cells. At the indicated time points, the total number of viable cells in each well was determined using a commercial MTT assay (Pierce) as per the manufacturer's recommendations.

Statistical Analysis: Statistical differences between different experimental groups were determined by log-rank and Student's t-test. The reported values represent the mean plus or minus the standard error of the mean. A P value of less than 0.05 was considered statistically significant.

As set forth above, GVHD is a potentially lethal clinical complication arising from the transfer of alloreactive T lymphocytes into immunocompromised recipients. Despite conventional methods of T cell depletion, GVHD remains a major challenge in allogeneic hematopoietic cell transplant. In the following examples, the inventors demonstrate a novel method of preventing GVHD by ex vivo treatment of primary human hematopoietic cells with Myxoma virus (MYXV). MYXV is known to have narrow host specificity for the European rabbit, and not to other species like mice and humans. The present inventors have found that MXYV treatment of human bone marrow and peripheral blood mononuclear cells, for example, did not inhibit human hematopoietic engraftment in immunocompromised mice; rather, ex vivo exposure of Myxoma virus to human grafts augmented human hematopoietic engraftment and increased post-transplant survival by eliminating graft versus host disease. Examination of major organs showed evidence for elimination of human T lymphocyte proliferation. MYXV also quelled mixed lymphocyte reactions by means of purging the alloreactive T cells. It is also noted that none of the profoundly immunocompromised mice had MYXV eruption. The following data suggest that ex vivo virotherapy with MYXV is a simple and effective method for preventing GVHD following infusion of hematopoietic products that potentially contain alloreactive lymphocytes, such as allogeneic hematopoietic stem and progenitor cells (HSPCs), donor leukocyte infusions and blood transfusions.

The present inventors have previously demonstrated the use of MYXV as a novel viral oncolytic agent for the treatment of a variety of human cancers while sparing normal human tissues (6-8). MYXV has several advantages as a virotherapeutic in humans. First, MYXV's natural host range is tightly restricted to rabbits. No instances of MYXV infection have been documented in any non-rabbit species, even after injection of live virus into human subjects and immunocompromised mice (9, 10). Second, MYXV does not depend on specific cell surface receptors for oncolysis, rather depends upon unique intracellular pathways such as AKT for permissinevess. This feature enables MYXV to effectively bind and purge a wide variety of human cancers. Finally, the therapeutic application of MYXV is relatively uncomplicated and quick, which makes it an attractive agent for clinical administration.

Recently, the present inventors demonstrated that ex vivo treatment of primary human hematopoietic cells contaminated with acute myeloid leukemia (AML) cells resulted in purging of the leukemic clone while sparing normal human HSPC (11). This selective purging, was not dependent on expression of any transgenes, addition of any chemotherapeutic agents, and required only a brief incubation of the graft sample with MYXV ex vivo prior to the transplant into immunocompromised NOD/scid/IL2R(gamma) (NSG) mice (11).

During the course of follow-up experiments into the use of MYXV as a clinical agent to purge various other human hematologic maligancies contaminating HSPC grafts, it was observed that 50-70% of sub-lethally irradiated NSG mice injected with healthy human bone marrow (BM) developed a lethal wasting disease 4-6 weeks after transplant (FIGS. 1A and 1B). This disease was not observed in mock injected irradiated control mice or in mice injected with established cancer cell lines, but was consistently observed following injection of BM obtained from three distinct healthy donors (Table 1 and FIG. 4). This disease was reminiscent of "secondary disease" described by Barnes and Loutit in the 1960's [PMID 13517181], which was later defined as GVHD. Consistent with GVHD, post-mortem histology of peripheral tissues from diseased mice revealed significant edema, as well as infiltration of human $CD3^+$ T lymphocytes into several organs, including the liver, intestines, skin, lung, kidney and spleen (FIG. 1C) (FIG. 4).

Unexpectedly, however, the present inventors have found that mice injected with healthy BM that had been pretreated ex vivo with MYXV universally survived without evidence for wasting (FIGS. 1A and 1B). Additional post-mortem histology revealed that mice injected with MYXV-treated bone marrow (BM) displayed virtually no infiltration of human $CD3^+$ T lymphocytes into any major organ, e.g., spleen, lung, liver, kidney (see e.g., FIG. 10 and FIG. 4). This data supports the novel observation that ex vivo treatment of allogeneic human hematopoietic cell grafts with MYXV can prevent GVHD and permit efficient engraftment of normal human HSPC.

Primary human BM contains $CD3^+$ T lymphocytes and $CD34^+$ HSPC. To determine if MYXV prevented the development of GVHD by affecting expansion of donor T lymphocytes or altering the long term engraftment of hematopoietic stem cells, we used immunomagnetic enrichment or depletion of $CD3^+$ T lymphocytes or $CD34^+$ HSPCs from primary human BM. Consistent with our diagnosis of GVHD, mice xenotransplanted with either positively selected $CD3^+$ lymphocytes or BM depleted of $CD34^+$ cells succumbed to GVHD with kinetics similar to mice transplanted with unfractionationed BM (Table 1). In contrast, mice transplanted with BM depleted of $CD3^+$ lymphocytes or positively selected $CD34^+$ HSPC failed to develop GVHD (Table 1). In all cohorts, NSG mice transplanted with human hematopoietic cells pretreated with MYXV universally survived and presented no evidence of GVHD.

With evidence that MYXV prevented donor T lymphocyte alloreactivity, it was next tested whether ex vivo MYXV treatment impaired HSPC engraftment. Specifically, xenotransplant models were used receiving whole BM, positively selected $CD34^+$ HSPC and $CD34^+$ depleted grafts. Consistent with previous observations (11), pretreatment of human hematopoietic grafts with MYXV did not significantly alter the proportion of mice with human hematopoietic engraftment six weeks after transplant (FIG. 2A). In mice transplanted with ex vivo treated whole BM, there was a trend towards decreased percentage of human hematopoietic engraftment in the bone marrow of mice. However, this trend did not reach statistical significance (FIG. 2B). In mice transplanted with ex vivo treated CD34+ HSPCs, there was no difference in percentage of human hematopoietic engraftment (FIG. 2D) and lineage analysis revealed multilineage engraftment with B lymphocyte skewing that is typically seen xenotransplanted mmunocompromised mice (FIG. 5). Mice transplanted with CD34+ depleted BM also showed evidence of human hematopoietic cell engraftment in the bone marrow six weeks after transplant. However, as expected, in comparison to the cohorts receiving whole BM and CD34+ HSPCs, the CD34+ depleted cohort showed lower levels of engraftment (FIG. 2C). Lineage analysis revealed multilineage engraftment with T lymphocyte skewing (FIG. 6). These data demonstrate that ex vivo MYXV treatment of human hematopoietic grafts does not impair human HSPC engraftment in immunocompromised recipients.

Figures 2E, 2F:
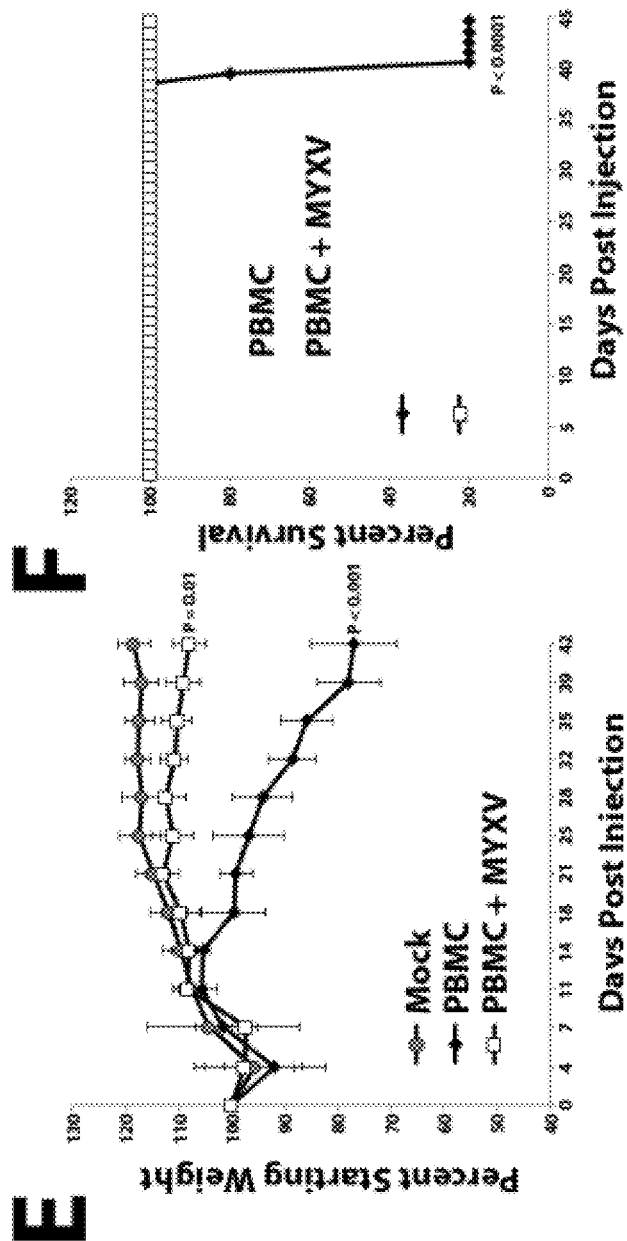

The results of GVHD in NSG mice after xenotransplant of human BM corroborates a recent report showing evidence of GVHD in NSG mice after xenotransplant of human peripheral blood mononuclear (PBMCs) (15). Unmobilized PBMC grafts contain high levels of CD3+ T lymphocytes and are used as T cell add-back in haploidential transplant protocols and donor leukocyte infusions. Clinically, the intent with PBMC infusions is to elicit graft-versus-leukemia (GVL) and provide anti-infection immunity; however, allogeneic PBMC infusions carry a high risk of GVHD. Given our results of Myxoma virus preventing GVHD after human BM transplant in immunocompromised mice, it was next tested whether Myxoma virus prevented GVHD associated with PBMC infusions. Consistent with previously published findings (15), NSG mice transplanted with human PBMCs showed significant weight loss (FIG. 2E) and succumbed to GVHD around 40 days after transplant (FIG. 2F). In contrast, mice transplanted with human PBMCs treated ex vivo with MYXV universally survived. These mice had a small but statistically significant weight loss, suggesting that virus treatment might only partially eliminate the potentially alloreactive T lymphocytes in this model.

Figure 3A:
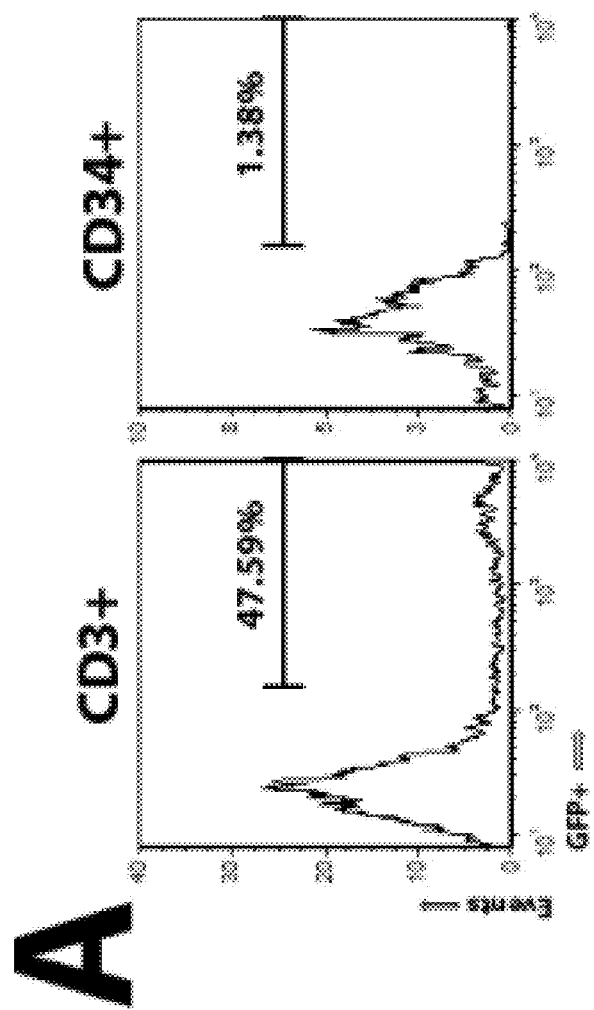
FIG. 3A-C: MYXV infects a subset of primary human $CD3^+$ T lymphocytes. To determine if MYXV could infect $CD3^+$ T lymphocytes found in BM, $1 \times 10^6$ whole BM cells were treated with vMYX-GFP at a Multiplicity of Infection (MOI)=10. Twenty-four hours after MYXV exposure, cells were stained with antibodies against either CD3 or CD34 and the levels of GFP+ cells in each population was determined using flow cytometry (A). To determine the variation in infection of $CD3^+$ lymphocytes between various bone marrow donors, 21 distinct bone marrow samples were infected and analyzed as above. The percent of $CD3^+$ lymphocytes that displayed expression of GFP+ ranged from 1%-47% (B). To determine if MYXV inhibited expansion of T lymphocyte following allo-stimulation, mock-treated MYXV-treated BM cells were incubated for 10 days with irradiated human leukocyte antigen (HLA)-mismatched feeder cells. Mock-treated BM stimulated with irradiated feeder cells showed significantly increased numbers of viable cells while MYXV-treated BM did not (C). Data shown represents the average of three independent experiments.
Figure 3B:
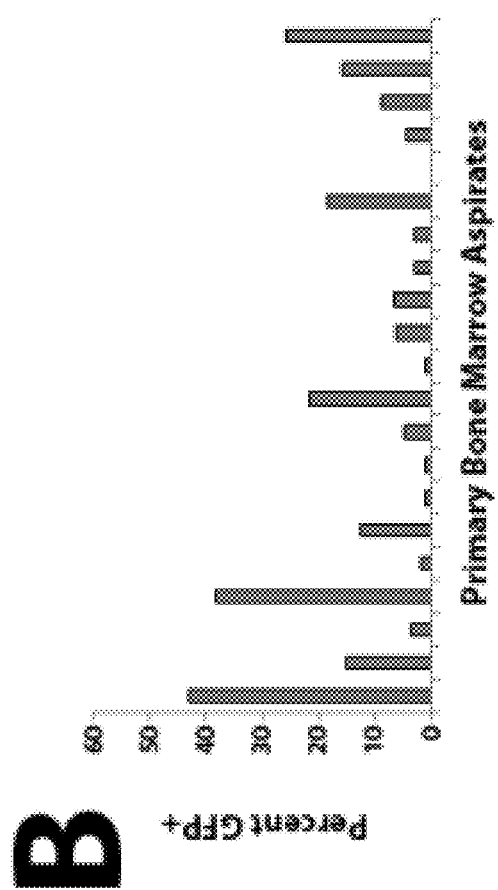
Figure 3C:
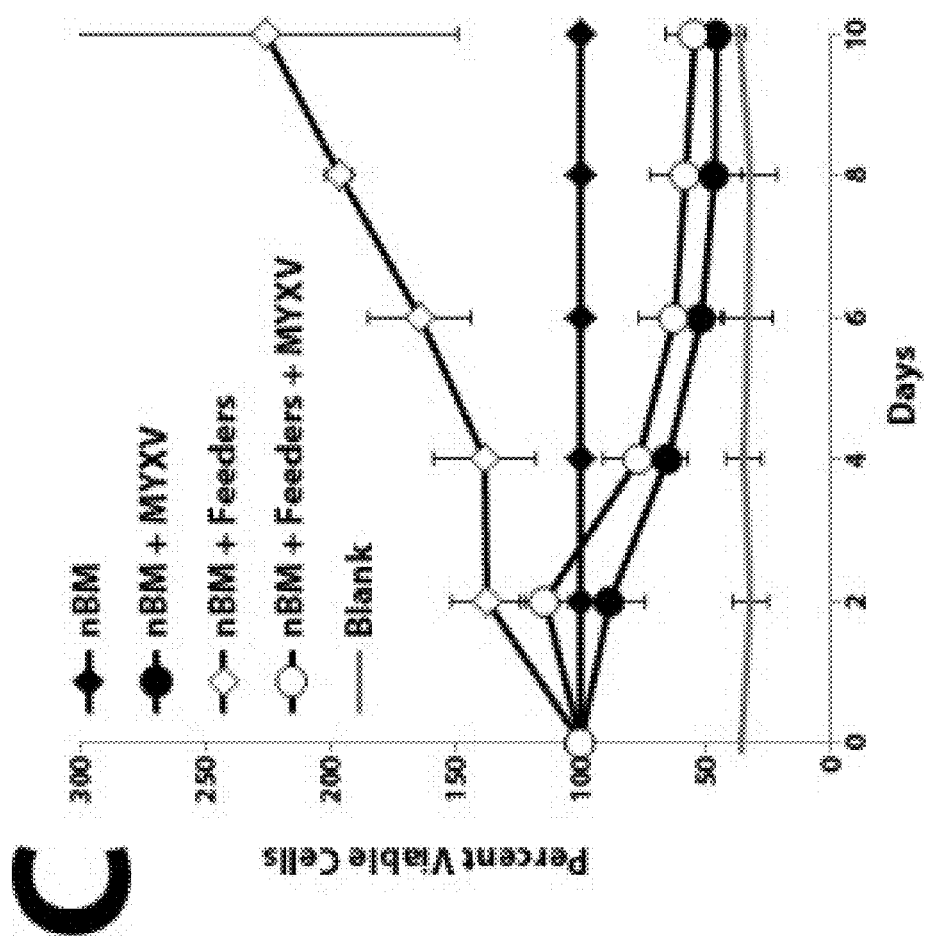
Figure 4A:
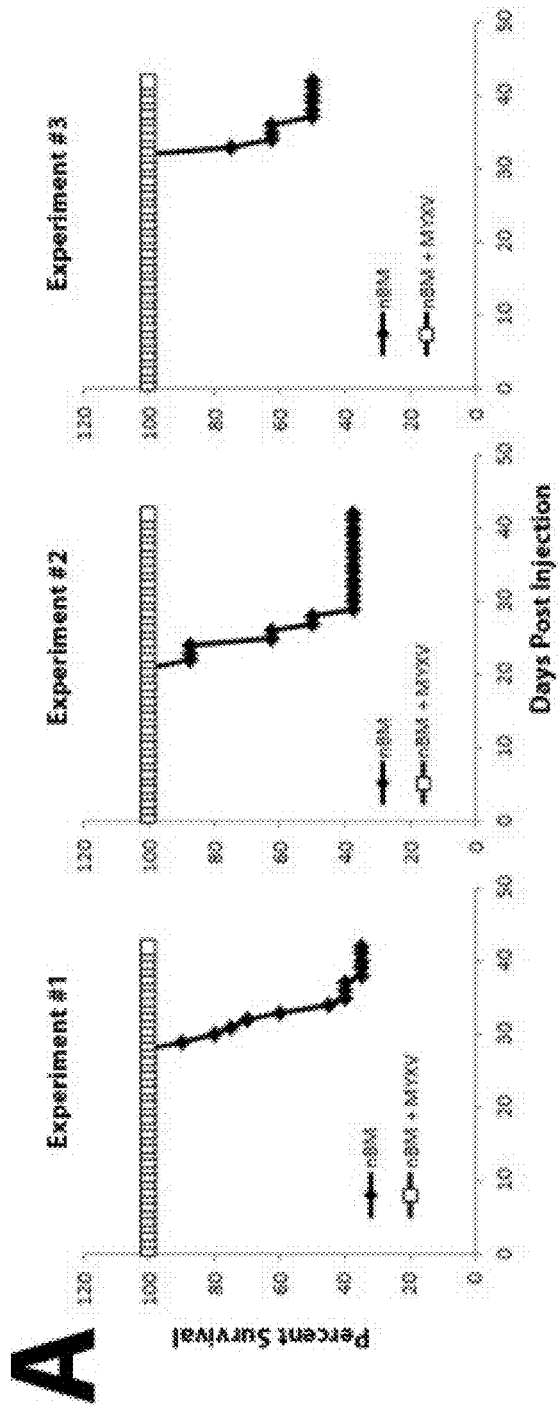
FIG. 4A-B: Development of GVHD is consistently observed between bone marrow donors. NSG mice were sublethally irradiated and then transplanted with $1 \times 10^7$ BM cells from three different donors (A). Mice were weighed twice per week to monitor body condition and sacrificed either six weeks post-injection or when they reached a body condition score of 2. Significant differences in survival were determined using the log-rank test (P<0.05). Post-mortem, organs were extracted, fixed in formalin, sectioned and stained for the presence of human CD3+ lymphocytes (B). Immunohistochemistry images shown are representative of results observed in five separate mice.
Figure 4B:
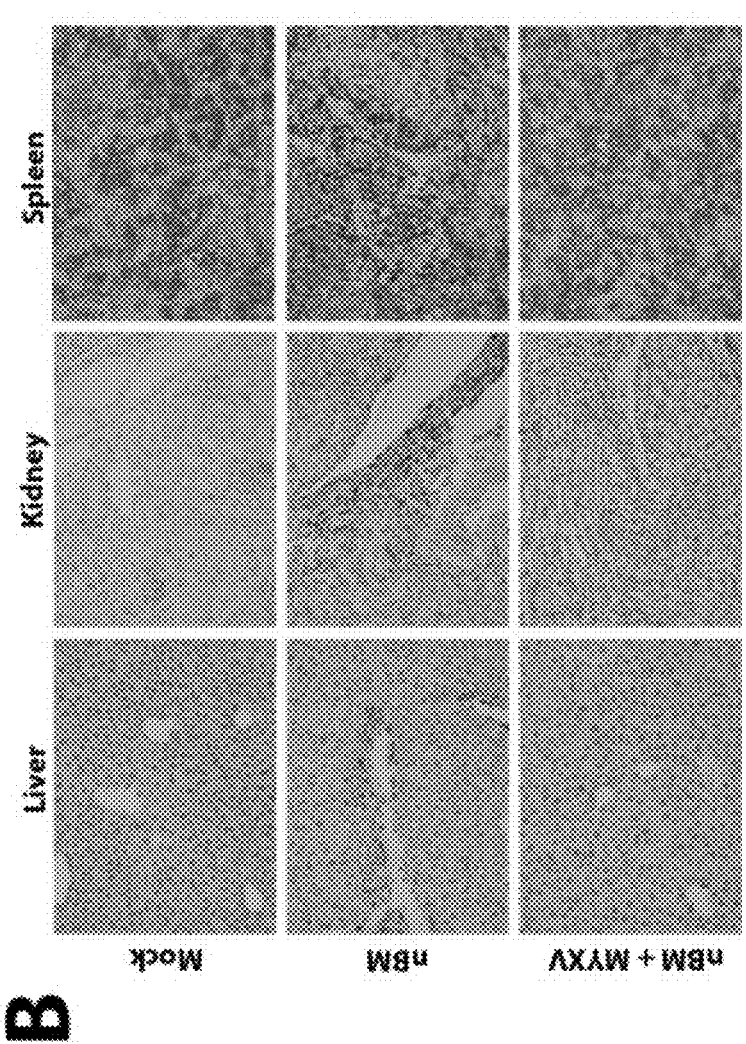
Figure 7:
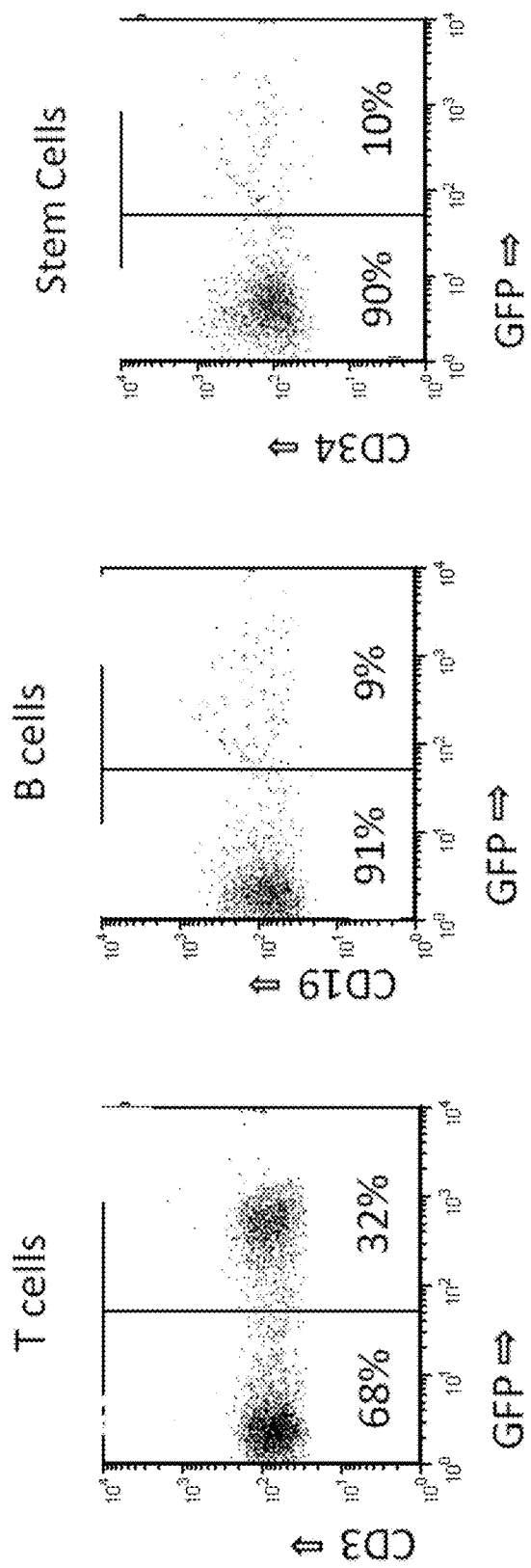
FIG. 7: Myxoma virus expressing GFP selectively infects a subset of primary T cells in normal bone marrow, but not CD19+ B cells or CD34+ stem cells.

With in vivo evidence that MYXV prevented GVHD after BM transplant and reduced GVHD after PBMC infusion, definition of the mechanism was sought by treating or contacting human BM with MYXV that expressed GFP from a synthetic early/late viral promoter (21). GFP expression, indicating MYXV infection, was observed in a small subset of CD3+ T lymphocytes, but was not found in any CD19+ B cells or CD34+ HSPCs (FIG. 3A and FIG. 7). Since MYXV treatment had proven remarkably consistent in its ability to prevent GVHD in vivo (FIG. 4), we were surprised to observe that the percent of CD3+ lymphocytes displaying evidence of MYXV infection varied greatly between various patient bone marrow samples (FIG. 3B). Thus, it was tested whether MYXV treatment might have a more consistent effect on T lymphocyte expansion induced by alloantigen stimulation in a one-way mixed lymphocyte reaction. It was found that mock-treated human BM showed a significant increase in viable cells when added to lethally irradiated HLA-mismatched human feeder cells. In contrast, pretreatment of the BM with MYXV prevented this MLR proliferation (FIG. 3C). This observation was consistent across three different patient bone marrow samples (FIG. 6). These data indicate that MYXV consistently inhibits expansion of alloreactive T lymphocytes from multiple primary donors even though MYXV infection rates of CD3+ lymphocytes in these samples appears to be highly variable.

Previously, it was demonstrated that MYXV treatment prevents engraftment of primary human AML stem and progenitor cells while sparing normal human HSPC (11). The data here presents an entirely novel application of MYXV, potentially administered in the setting where allogeneic hematopoietic cells are infused such as alloHCT, PBMC infusions and supportive blood product transfusions. The data demonstrating the prevention of GVHD by Myxoma virus treatment is the first report of such a strategy, which exploits an intact replicating oncolytic virus to prevent development of an autoimmune disease. It should be noted that removal of alloreactive T lymphocytes from alloHCT samples is a fundamentally similar process to purging cancer cells from autologous hematopoietic cell grafts. Both are based on the ability of the purging agent (Myxoma virus) to distinguish the contaminating cells (either cancer cells in autologous grafts or donor T lymphocytes in allogeneic grafts) from the stem cells whose function must be maintained (in this case, hematopoietic stem cells). A variety of viruses currently under investigation for use as oncolytic agents have evolved various methods to distinguish one cell type from another. The data presented here suggest that the potential therapeutic uses of some oncolytic viruses, like MYXV, could be expanded to the treatment of non-malignant disease such as T lymphocyte or B lymphocyte mediated autoimmune disorders. Various lymphocyte purging methods, including positive or negative cell separation as well as treatment with specific cytotoxic agents, have been previously attempted to improve alloHCT for treatment of hematologic malignancies. These methods, however, carry high risks of life-threatening infections due to delayed immunologic recovery and graft failure (4, 5). The data here show that MYXV treatment appears to have no adverse effects on normal HSPC engraftment and due to the infection of a subset of alloreactive CD3+ T lymphocytes, might still allow for the adoptive transfer of a functional lymphocyte subset for immediate anti-infective and anti-cancer intent into the recipient. Additionally, MYXV treatment requires only a single, brief virus adsorption step prior to graft infusion which could be performed in current good tissue practice (GTP) clinical conditions (11). Therefore, translating the observation that MYXV treatment prevents GVHD into a clinical setting would not require significant deviation from the current standard of care for alloHCT, PBMC infusions and blood transfusions.

While not wishing to be bound by theory, it is believed that the mechanism of MYXV's ability to discriminate alloreactive T lymphocytes from other T lymphocyte subsets and HSPCs and its safety for MYXV in terms of human hematopoietic engraftment might be based on a failure of MYXV to bind to normal human CD34+ HSPCs. Due to the extremely broad nature of poxvirus binding for most mammalian cells (18) this suggests that MYXV might be an effective agent for functionally deleting a wide variety of non-stem cells from hematopoietic graft including donor T lymphocytes as well as contaminating cancer cells from a wide variety of hematopoietic malignancies. Interestingly, in the current study, we observed that whereas only a small subset of CD3+ T lymphocytes were infected by MYXV, the virus completely abrogated GVHD in every xenotransplant. This selective infection could allow MYXV to inhibit GVHD while still allowing adoptive transfer of some functional T lymphocytes into the alloHCT recipient, thus providing beneficial antimicrobial and anticancer immunity (19). Considering that MYXV can elicit oncolytic activity by merely binding and not necessarily infecting cancer cells (20), it also possible that MYXV might prevent GVHD by simply inhibiting the post-transplant expansion of a selective subpopulation of CD3+ lymphocytes in the absence of a fully productive virus infection. In any event, ex vivo MYXV virotherapy prior to infusion of allogeneic hematopoietic cells offers not only the prospect of preventing the onset of GVHD and reducing the risks of severe disease, but also permits the opportunity for transplant of allogeneic grafts with greater HLA disparity such as those from mismatched unrelated donors and haploidentical donors, thereby opening up alloHCT to a greater number of patients.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

REFERENCES

1. S. W. Choi, J. E. Levine, J. L. Ferrara, *Immunol Allergy Clin North Am* 30, 75 (February).
2. B. R. Blazar, R. Korngold, D. A. Vallera, *Immunol Rev* 157, 79 (June, 1997).
3. S. Paczesny, S. W. Choi, J. L. Ferrara, *Curr Opin Hematol* 16, 427 (November, 2009).
4. P. J. Martin et al., *Bone Marrow Transplant* 3, 445 (September, 1988).
5. M. Delain et al., *Leuk Lymphoma* 11, 359 (November, 1993).
6. M. M. Stanford et al., *Mol Ther* 16, 52 (January, 2008).
7. Y. Woo et al., *Ann Surg Oncol* 15, 2329 (August, 2008).
8. X. Q. Lun et al., *Cancer Res* 67, 8818 (Sep. 15, 2007).
9. F. Fenner, F. N. Ratcliffe, *Myxomatosis*. (Cambridge University Press, Cambridge, UK, 1965).
10. M. M. Stanford, G. McFadden, *Expert Opin Biol Ther* 7, 1415 (September, 2007).
11. M. Kim et al., *Leukemia* 23, 2313 (December, 2009).
12. A. Gratwohl et al., *Bone Marrow Transplant* 41, 687 (April, 2008).
13. D. Gallardo et al., *Haematologica* 94, 1282 (September, 2009).
14. J. Tanaka, *Rinsho Ketsueki* 43, 442 (June, 2002).
15. R. Ito et al., *Transplantation* 87, 1654 (Jun. 15, 2009).
16. R. K. Burt et al., *J Autoimmun* 30, 116 (May, 2008).
17. C. Annaloro, F. Onida, G. Lambertenghi Deliliers, *Expert Rev Hematol* 2, 699 (December, 2009).
18. B. Moss, in *Fields Virology*, D. M. K. a. P. M. Howley, Ed. (Lippincott, Williams & Wilkins, New York 2007), vol. 2, pp. p. 2849-2855.
19. J. W. Hiemenz, *Semin Hematol* 46, 289 (July, 2009).
20. G. Madlambayan et al., *Cancer Res* Submitted, (2011).
21. J. B. Johnston et al., *J Virol* 77, 5877 (May, 2003).

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

The invention claimed is:

1. A method of treating cancer in a subject comprising:
   a) admixing ex vivo a graft comprising a plurality of hematopoietic cells with an amount of Myxoma Virus effective to inhibit proliferation of T lymphocytes in said graft; and
   b) administering said admixed graft to a subject, such that said cancer is treated, wherein the graft is allogeneic with respect to the subject.

2. The method of claim 1 wherein said graft comprises bone marrow or human peripheral blood cells.

3. The method of claim 1 wherein said graft comprises T lymphocytes.

4. The method of claim 3, wherein said T lymphocytes comprise CD45+ cells.

5. The method of claim 3, wherein said T lymphocytes comprise CD3+ cells.

6. The method of claim 1, wherein the Myxoma Virus is admixed with hematopoietic cells at a ratio of 10:1 (infectious virus:nucleated cells).

7. The method of claim 1, wherein said cancer is selected from the group consisting of hematological malignancies, neuroblastoma, sarcomas, lung cancer, small cell lung cancer, breast cancer, colorectal cancer, pancreatic cancer, brain cancer, ovarian cancer and gastric cancer.

8. The method of claim 7, wherein the hematological malignancy comprises leukemia, a myelodysplastic syndrome, a lymphoma, or a myeloma.

9. The method of claim 8, wherein the hematological malignancy comprises acute myeloid leukemia (AML) or multiple myeloma (MM).

10. A method for inhibiting the proliferation of T lymphocytes in a biological sample comprising contacting the biological sample with an amount of Myxoma Virus effective to inhibit the proliferation of T lymphocytes post-transplant in said biological sample, wherein the biological sample is human.

11. The method of claim 10, wherein the biological sample comprises a bone marrow sample or a blood sample.

12. The method of claim 11 wherein the blood sample is human peripheral blood cells.

13. The method of claim 11 wherein said blood sample comprises T lymphocytes.

14. The method of claim 13, wherein said T lymphocytes comprise CD45+ cells.

15. The method of claim 13, wherein said T lymphocytes comprise CD3+ cells.

16. The method of claim 10 wherein the Myxoma Virus is admixed with the biological sample at a ratio of 10:1 (infectious virus: nucleated cells).

17. A composition, comprising human hematopoietic cells admixed with Myxoma Virus; wherein said Myxoma Virus is admixed with the hematopoietic cells at a ration of 10:1 (infectious virus:nucleated cells).

18. The compositions according to claim 17, wherein said hematopoietic cells are within human peripheral blood, bone marrow, or umbilical cord blood specimens.

19. The composition according to claim 18 wherein said hematopoietic cells comprise T lymphocytes.

20. The composition according to claim 18 wherein said hematopoietic cells comprise CD45+ cells.

21. The composition according to claim 18 wherein said hematopoietic cells comprise CD3+ cells.

22. A method of treating an autoimmune disorder in a subject comprising:
   admixing ex vivo a graft comprising a plurality of hematopoietic cells with an amount of Myxoma Virus effective to inhibit proliferation of pathogenic, auto-reactive T lymphocytes in said graft; and
   administering said admixed graft to a subject.

23. The method of claim 22, wherein said graft comprises bone marrow.

24. The method of claim 22, wherein said graft comprises human peripheral blood cells.

25. The method of claim 22, wherein said graft comprises a reduced amount of T lymphocytes.

26. A method for inhibiting the proliferation of CD3+T lymphocytes in a human biological sample comprising contacting the human biological sample with an amount of Myxoma Virus effective to inhibit the proliferation of the CD3+T lymphocytes in the human biological sample.

27. The method of claim 26, wherein the CD3+T lymphocytes are alloreactive or auto-reactive.

* * * * *